United States Patent [19]

Regel et al.

[11] 4,174,398
[45] Nov. 13, 1979

[54] COMBATING FUNGI WITH 1-ALKYL-1-(1,3,4-THIADIAZOL-2-YL)-3-PHENYL-UREAS

[75] Inventors: Erik Regel, Wuppertal; Paul-Ernst Frohberger, Leverkusen; Volker Paul, Solingen, all of Fed. Rep. of Germany

[73] Assignee: Bayer Aktiengesellschaft, Leverkusen, Fed. Rep. of Germany

[21] Appl. No.: 882,833

[22] Filed: Mar. 2, 1978

[30] Foreign Application Priority Data

Mar. 23, 1977 [DE] Fed. Rep. of Germany ....... 2712630

[51] Int. Cl.² ............... A01N 9/12; C07D 285/12
[52] U.S. Cl. ............... 424/270; 260/453 AR; 560/103; 560/104; 548/140; 548/138
[58] Field of Search ................. 260/306.8 D; 424/270

[56] References Cited

U.S. PATENT DOCUMENTS

| | | | |
|---|---|---|---|
| 3,772,316 | 11/1973 | Wakae et al. ................. | 260/306.8 D |
| 3,990,879 | 11/1976 | Soper ....................... | 71/66 |

FOREIGN PATENT DOCUMENTS

| | | | |
|---|---|---|---|
| 1901672 | 11/1969 | Fed. Rep. of Germany ... | 260/306.8 D |
| 1770467 | 11/1971 | Fed. Rep. of Germany ... | 260/306.8 D |
| 51-00611 | 1/1976 | Japan ...................... | 260/306.8 D |

OTHER PUBLICATIONS

Yamazaki et al., Chem. Abstracts, vol. 85, Abstract No. 105418a (1976).
Grant et al., J. Med. Chem., vol. 15, pp. 1082–1084 (1972).

Primary Examiner—Alton D. Rollins
Attorney, Agent, or Firm—Sprung, Felfe, Horn, Lynch & Kramer

[57] ABSTRACT

1-Alkyl-1-(1,3,4-thiadiazol-2-yl)-3-phenyl-ureas of the formula

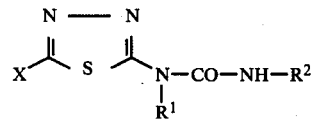

in which
R¹ is alkyl,
R² is phenyl or substituted phenyl, and
X is hydrogen or halogen,
which possess fungicidal properties.

3 Claims, No Drawings

COMBATING FUNGI WITH 1-ALKYL-1-(1,3,4-THIADIAZOL-2-YL)-3-PHENYL-UREAS

The present invention relates to and has for its objects the provision of particular new 1-alkyl-1-(1,3,4-thiadiazol-2-yl)-3-phenyl-ureas which possess fungicidal properties, active compositions in the form of mixtures of such compounds with solid and liquid dispersible carrier vehicles, and methods for producing such compounds and for using such compounds in a new way especially for combating fungi, with other and further objects becoming apparent from a study of the within specification and accompanying examples.

The present invention relates to certain new 1,3,4-thiadiazol-2-yl-ureas, to a process for their preparation and to their use as fungicides.

It has already been disclosed that zinc ethylene-1,2-bis-dithiocarbamate ("Zineb") is a good agent for combating fungal plant diseases (see Phytopathology 33, 113 (1963)). However, its use as a seed dressing is possible only to a limited extent, since its activity is slight when low application amounts and concentrations are used.

The present invention now provides, as new compounds, the 1,3,4-thiadiazol-2-yl-ureas of the general formula

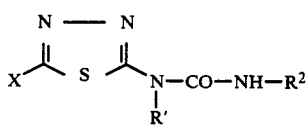

in which
R$^1$ represents alkyl,
R$^2$ represents phenyl or monosubstituted or polysubstituted phenyl, and
X represents hydrogen or halogen,
Preferably, R$^1$ represents straight-chain or branched alkyl with 1 to 12 carbon atoms; X represents hydrogen, chlorine or bromine; and R$^2$ represents monosubstituted or polysubstituted phenyl, the substituents being selected, independently of one another, from nitro, cyano, halogen (especially fluorine, chlorine or bromine), straight-chain or branched alkyl with 1 to 4 carbon atoms, alkoxy and alkylthio each with 1 to 4 carbon atoms, halogenoalkyl, halogenoalkyloxy and halogenoalkylthio with, in each case, up to 4 carbon atoms and up to 5 halogen atoms (especially with up to 2 carbon atoms and up to 3 identical or different halogen atoms, preferred halogen atoms being fluorine and chlorine, and examples of such substituents which may be mentioned being trifluoromethyl, trifluoromethoxy, trifluoromethylthio, chloromethyl, chloromethoxy and chloromethylthio), alkoxycarbonyl and alkoxycarbonylalkyl each with 1 to 4 carbon atoms in each alkyl part, alkoxycarbonylalkenyl with 1 to 4 carbon atoms in the alkyl part and 2 to 4 carbon atoms in the alkenyl part, dialkylamino with 1 to 2 carbon atoms in each alkyl part, alkoxycarbonyl-alkylamino with 1 or 2 carbon atoms in each alkyl part, and phenyl and phenoxy either of which is optionally substituted by halogen (especially fluorine, chlorine or bromine), by alkyl with 1 to 2 carbon atoms or by halogenoalkyl with up to 3 halogen atoms and 1–4 carbon atoms.

Surprisingly, in contrast to the compounds in which X represents alkylsulphonyl or trifluoromethyl and which are known as herbicides (see, for example, DT-OS (German Published Specification) No. 1,901,672 or DT-OS (German Published Specification) No. 1,770,467,) the 1,3,4-thiadiazol-2-yl-ureas according to the invention exhibit no herbicidal properties. In addition, it is surprising that the 1,3,4-thiadiazol-2-yl-ureas according to the invention exhibit a considerably higher fungicidal activity, in particular towards cereal diseases, than zinc ethylene-1,2-bis-dithiocarbamate, which is a known substance of the same type of action. The active compounds according to the invention thus represent an enrichment of the art.

The invention also provides a process for the preparation of a 1,3,4-thiadiazol-2-yl-urea of the formula (I), in which a 2-alkylamino-1,3,4-thiadiazole of the general formula

in which
R$^1$ and X have the meanings stated above,
is reacted with an isocyanate of the general formula

in which
R$^2$ has the meaning stated above,
in the presence of a diluent and optionally in the presence of a catalyst.

The starting substances of the formula (II) can also exist as 2-alkylamino-1,3,4-thiadiazoles of the formula

(see Chem. Berichte 27, 622 (1894)), which, however, is not significant for the compounds of the formula (I) according to the invention.

If 2-methylamino-1,3,4-thiadiazole and 4-chlorophenyl isocyanate are used as starting materials, the course of the reaction can be represented by the following equation:

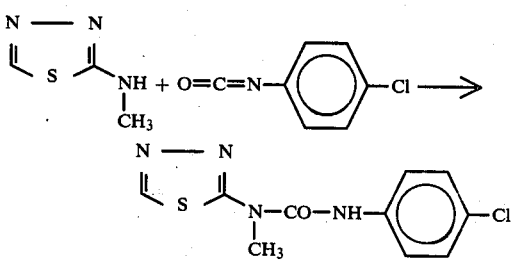

Examples of the starting materials of the formula (II) are: 2-methylamino-1,3,4-thiadiazole, 5-fluoro-2-methylamino-1,3,4-thiadiazole, 5-chloro-2-methylamino-1,3,4-thiadiazole, 5-bromo-2-methylamino-1,3,4-thiadiazole, 5-iodo-2-methylamino-1,3,4-thiadiazole, 5-chloro-2-ethylamino-1,3,4-thiadiazole, 5-bromo-2-ethylamino-1,3,4-thiadiazole, 5-chloro-2-propylamino-1,3,4-thiadiazole, 5-bromo-2- propylamino-1,3,4-thiadiazole, 5-chloro-2-isopropylamino-1,3,4-thiadiazole, 5-bromo-2-isopropylamino-1,3,4-thiadiazole, 5-chloro-2-butylamino-1,3,4-thiadiazole, 5-bromo-2-butylamino-1,3,4-thiadiazole, 5-chloro-2-isobutylamino-1,3,4-thiadiazole, 5-bromo-2-isobutylamino-1,3,4-thiadiazole, 5-chloro-2-tert.-butylamino-1,3,4-thiadiazole and 5-bromo-2-tert.-butylamino-1,3,4-thiadiazole.

Those 2-alkylamino-1,3,4-thiadiazoles of the formula (II) in which X represents hydrogen are known (see J. Org. Chem. 38, 3949 (1973)). On the other hand, the 5-halogeno-2-alkylamino-1,3,4-thiadiazoles of the formula (II) have not yet been described in the literature. However, they can be prepared by processes which are known in principle (see German Offenlegungsschriften (German Published Specification) No. 2,435,005 and U.S. Pat. No. 3,830,925). Thus, for example, a 5-bromo-2-alkylamino-1,3,4-thiadiazole is obtained by treating a 2-alkylamino-1,3,4-thiadiazole, in acetic acid, with bromine at temperatures from 20° to 60° C., and a 5-chloro-2-alkylamino-1,3,4-thiadiazole is obtained by subsequently reacting the bromine compound with dilute hydrochloric acid at temperatures from 80° to 120° C. (see also the preparative Examples given later in this text).

Those compounds of the general formula (II) in which X represents chlorine or bromine are particularly interesting new intermediates; new secondary products can be prepared by reaction with isocyanates or also carboxylic acid derivatives which react with the 2-aminoalkyl group.

Examples of the starting materials of the formula (III) are: phenyl isocyanate, 4-chlorophenyl isocyanate, 3-chlorophenyl isocyanate, 2-chlorophenyl isocyanate, 4-fluorophenyl isocyanate, 3-fluorophenyl isocyanate, 2-fluorophenyl isocyanate, 2,4-dichlorophenyl isocyanate, 2,3-dichlorophenyl isocyanate, 2,5-dichlorophenyl isocyanate, 2,6-dichlorophenyl isocyanate, 4-chloro-2-methyl-phenyl isocyanate, 2-chloro-4-methyl-phenyl isocyanate, 2-chloro-5-methyl-phenyl isocyanate, 4-chloro-2-ethyl-phenyl isocyanate, 4-methylphenyl isocyanate, 3-methylphenyl isocyanate, 2-methylphenyl isocyanate, 4-trifluoromethylphenyl isocyanate, 3-trifluoromethylphenyl isocyanate, 2-trifluoromethylphenyl isocyanate, 3-chloromethylphenyl isocyanate, 2-chloro-4-trifluoromethyl-phenyl isocyanate, 4-trifluoromethoxyphenyl isocyanate, 4-trifluoromethylthio-phenyl isocyanate, 4-methoxyphenyl isocyanate, 4-ethoxyphenyl isocyanate, 4-methylthiophenyl isocyanate, 4-ethylthiophenyl isocyanate, 3,4-dichloro-5-methylphenyl isocyanate, 3-chloromethyl-4-chlorophenyl isocyanate, 3-(2-chloroethyl)-phenyl isocyanate, 3-methoxycarbonyl-phenyl isocyanate, 3-butoxycarbonyl-phenyl isocyanate, 3-dimethylaminophenyl isocyanate, 3-(methyl-methoxycarbonyl-amino)-phenyl isocyanate, 3-ethoxycarbonylvinyl-phenyl isocyanate, 4-(4-chlorophenyl)-phenyl isocyanate, 4-(4-chlorophenoxy)-phenyl isocyanate, 4-nitrophenyl isocyanate, 3-nitrophenyl isocyanate and 4-cyanophenyl isocyanate.

Isocyanates of the formula (III) are known and can be prepared by processes which are generally customary and known, for example by reacting amines or amides with phosgene or, respectively, oxalyl chloride, and subsequently heating the product.

Preferred diluents which can be used for the reaction according to the invention are the inert organic solvents, especially nitriles, such as propionitrile and, in particular, acetonitrile; ethers, such as tetrahydrofuran or dioxane formamides, such as, in particular, dimethylformamide; hydrocarbons, such as, in particular, toluene; halogenated hydrocarbons, such as methylene chloride, carbon tetrachloride, chloroform or chlorobenzene; and esters, such as, in particular, ethyl acetate.

Preferred catalysts which can be used are tertiary bases, such as triethylamine and pyridine, or organo-tin compounds, such as dibutyl-tin dilaurate.

The reaction temperatures can be varied within a relatively wide range. In general, the reaction is carried out at from 0° to 120° C., preferably at from 20° to 100° C. The reaction is appropriately carried out at the boiling point of the particular solvent.

In carrying out the process according to the invention, equimolar amounts are preferably used. The compounds of the formula (I) are isolated in the customary manner.

Examples of particularly active compounds according to the invention are the following: 1-(5-chloro-1,3,4-thiadiazol-2-yl)-1-methyl-3-phenyl-urea, 1-(5-chloro-1,3,4-thiadiazol-2-yl)-1-methyl-3-(4-chloro-3-methylphenyl)-urea, 1-(5-chloro-1,3,4-thiadiazol-2-yl)-1-methyl-3-(3-chloro-4-methylphenyl)-urea, 1-(5-chloro-1,3,4-thiadiazol-2-yl)-1-methyl-3-(2-chlorophenyl)-urea, 1-(5-chloro-1,3,4-thiadiazol-2-yl)-1-methyl-3-(3-trifluoromethylphenyl)-urea, 1-(5-chloro-1,3,4-thiadiazol-2-yl)-1-methyl-3-(2,4-dichlorophenyl)-urea, 1-(5-chloro-1,3,4-thiadiazol-2-yl)-1-methyl-3-(2-chloro-5-methylphenyl)-urea, 1-(5-chloro-1,3,4-thiadiazol-2-yl)-1-methyl-3-(4-chloro-2-methylphenyl)-urea, 1-(5-chloro-1,3,4-thiadiazol-2-yl)-1-methyl-3-(3-methylphenyl)-urea, 1-(5-chloro-1,3,4-thiadiazol-2-yl)-1-methyl-3-(4-methylphenyl)-urea, 1-(5-chloro-1,3,4-thiadiazol-2-yl)-1-methyl-3-(4-fluorophenyl)-urea, 1-(5-chloro-1,3,4-thiadiazol-2-yl)-1-methyl-3-(4-chloro-3-trifluoromethylphenyl)-urea, 1-(5-chloro-1,3,4-thiadiazol-2-yl)-1-methyl-3-(4-trifluoromethylthiophenyl)-urea, 1-(5-chloro-1,3,4-thiadiazol-2-yl)-1-methyl-3-(3-butoxycarbonylphenyl)-urea, 1-(5-bromo-1,3,4-thiadiazol-2-yl)-1-methyl-3-phenyl-urea, 1-(5-bromo-1,3,4-thiadiazol-2-yl)-1-methyl-3-(4-chloro-3-methylphenyl)-urea, 1-(5-bromo-1,3,4-thiadiazol-2-yl)-1-methyl-3-(3-chloro-4-methylphenyl)-urea, 1-(5-bromo-1,3,4-thiadiazol-2-yl)-1-methyl-3-(2-chlorophenyl)-urea, 1-(5-bromo-1,3,4-thiadiazol-2-yl)-1-methyl-3-(3-trifluoromethylphenyl)-urea, 1-(5-bromo-1,3,4-thiadiazol-2-yl)-1-methyl-3-(2,4-dichlorophenyl)-urea, 1-(5-bromo-1,3,4-thiadiazol-2-yl)-1-methyl-3-(2-chloro-5-methyl-phenyl)-urea, 1-(5-bromo-1,3,4-thiadiazol-2-yl)-1-methyl-3-(4-chloro-5-methylphenyl)-urea, 1-(5-bromo-1,3,4-thiadiazol-2-yl)-1-methyl-3-(3-methylphenyl)-urea, 1-(5-bromo-1,3,4-thiadiazol-2-yl)-1-methyl-3-(4-methylphenyl)-urea, 1-(5-bromo-1,3,4-thiadiazol-2-yl)-1-methyl-3-(4-fluorophenyl)-urea, 1-(5-bromo-1,3,4-thiadiazol-2-yl)-1-methyl-3-(4-chloro-3-trifluoromethylphenyl)-urea, 1-(5-bromo-1,3,4-thiadiazol-2-yl)-1-methyl-3-(4-trifluoromethylthiophenyl)-urea, 1-(5-bromo-1,3,4-thiadiazol-2-yl)-1-methyl-3-(3-butoxycarbonylphenyl)-urea, 1-ethyl-1-(1,3,4-thiadiazol-2-yl)-3-phenyl-urea, 1-ethyl-1-(1,3,4-thiadiazol-2-yl)-3-(2,4-dichlorophenyl)-urea, 1-ethyl-1-(1,3,4-thiadiazol-2-yl)-3-(4-methylphenyl)-urea, 1-ethyl-1-(1,3,4-thiadiazol-2-yl)-3-(4-fluorophenyl)-urea, 1-propyl-1-(1,3,4-thiadiazol-2-yl)-3-phenyl-urea, 1-propyl-1-(1,3,4-thiadiazol-2-yl)-3-(2,4-dichlorophenyl)-urea, 1-propyl-1-(1,3,4-thiadiazol-2-yl)-3-(4-methylphenyl)-urea, 1-propyl-1-(1,3,4-thiadiazol-2-yl)-3-(4-fluorophenyl)-urea, 1-ethyl-1-(5-chloro-1,3,4-thiadiazol-2-yl)-3-phenyl-urea, 1-ethyl-1-(5-chloro-1,3,4-thiadiazol-2-yl)-3-

(2,4-dichlorophenyl)-urea, 1-ethyl-1-(5-chloro-1,3,4-thiadiazol-2-yl)-3-(4-methylphenyl)-urea, 1-ethyl-1-(5-chloro-1,3,4-thiadiazol-2-yl)-3-(4-fluorophenyl)-urea, 1-ethyl-1-(5-chloro-1,3,4-thiadiazol-2-yl)-3-(4-chlorophenyl)-urea, 1-ethyl-(5-bromo-1,3,4-thiadiazol-2-yl)-3-phenyl-urea, 1-ethyl-(5-bromo-1,3,4-thiadiazol-2-yl)-3-(2,4-dichlorophenyl)-urea, 1-ethyl-(5-bromo-1,3,4-thiadiazol-2-yl)-3-(4-methylphenyl)-urea, 1-ethyl-(5-bromo-1,3,4-thiadiazol-2-yl)-3-(4-fluorophenyl)-urea, 1-ethyl-(5-bromo-1,3,4-thiadiazol-2-yl)-3-(4-chlorophenyl)-urea, 1-isopropyl-1-(1,3,4-thiadiazol-2-yl)-3-(4-chlorophenyl)-urea, 1-butyl-1-(1,3,4-thiadiazol-2-yl)-3-(4-chlorophenyl)-urea, 1-isobutyl-1-(1,3,4-thiadiazol-2-yl)-3-(4-chlorophenyl)-urea, 1-sec.-butyl-1-(1,3,4-thiadiazol-2-yl)-3-(4-chlorophenyl)-urea, 1-tert.-butyl-1-(1,3,4-thiadiazol-2-yl)-3-(4-chlorophenyl)-urea, 1-hexyl-1-(1,3,4-thiadiazol-2-yl)-3-(4-chlorophenyl)-urea, and 1-dodecyl-1-(1,3,4-thiadiazol-2-yl)-3-(4-chlorophenyl)-urea.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

As plant protection agents, the compounds according to the invention can be used for the treatment of soil, for the treatment of seed and for the treatment of above-ground parts of plants.

When used as seed dressings, the compounds according to the invention are active against seed-borne fungal plant diseases, in particular through disinfecting the surface of the seed, for example against stripe disease of barley, as well as systemically against fungal pathogens in the interior of the seed, as in the case of loose smuts of wheat and of barley. Furthermore, a systemic protective action against fungal infections of the shoot, for example against mildew, is achieved by seed dressing.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention can be present in the formulations as a mixture with other active compounds, such as fungicides, insecticides, acaricides, nematicides, herbicides, bird repellents, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001 percent.

In the treatment of seed, amounts of active compound of 0.001 to 50 g, preferably 0.01 to 10 g, are generally employed per kilogram of seed.

In the case of somewhat higher concentrations, growth-regulating properties are also displayed.

The present invention also provides fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

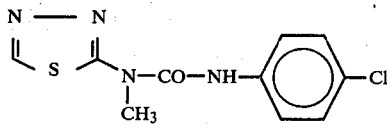 (1)

153.5 g (1 mol) of 4-chlorophenyl isocyanate in 500 ml of acetonitrile were added dropwise to 115 g (1 mol) of 2-methylamino-1,3,4-thiadiazole in 1,000 ml of acetonitrile, whereupon the temperature rose to 60° C. After adding 1 ml of triethylamine, the reaction mixture was heated under reflux for 12 hours. Thereafter, it was allowed to cool, and the crystalline precipitate was filtered off. This gave 122.5 g (83.5% of theory) of 1-methyl-1-(1,3,4-thiadiazol-2-yl)-3-(4-chlorophenyl)-urea of melting point 182° C.

EXAMPLE 2

(a)

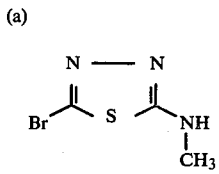

50 ml (1 mol) of bromine were added dropwise to 115 g (1 mol) of 2-methylamino-1,3,4-thiadiazole in 500 ml of glacial acetic acid, while stirring, whereupon the temperature rose to 55° C. The mixture was stirred for a further 1 hour. After adding 80 g (1 mol) of sodium acetate in 800 ml of water, the mixture was stirred overnight. The precipitate was filtered off, washed with water and dried. This gave 179.5 g (92.5% of theory) of 5-bromo-2-methylamino-1,3,4-thiadiazole of melting point 124° C.

(b) (2)

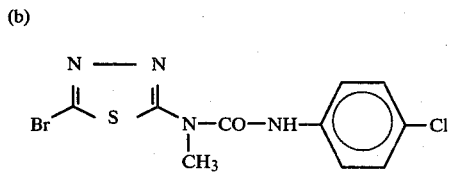

46 g (0.3 mol) of 4-chlorophenyl isocyanate in 100 ml of acetonitrile were added dropwise to 58.2 g (0.3 mol) of 5-bromo-2-methylamino-1,3,4-thiadiazole in 500 ml of acetonitrile. After adding 1 ml of triethylamine, the reaction mixture was heated under reflux for 12 hours. After cooling, the crystals which had separated out were filtered off and dried. This gave 96.5 g (92% of theory) of 1-(5-bromo-1,3,4-thiadiazol-2-yl)-1-methyl-3-(4-chlorophenyl)-urea of melting point 250° C.

EXAMPLE 3

(a)

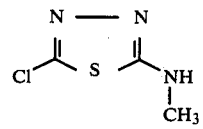

38.8 g (0.2 mol) of 5-bromo-2-methylamino-1,3,4-thiadiazole (Example 2a) were heated for 12 hours in 800 ml of 20% strength hydrochloric acid. The reaction mixture was concentrated in vacuo, and ethyl acetate was added to the residue. The crystals which precipitated were filtered off and suspended in 400 ml of acetonitrile, and 20.2 g (0.2 mol) of triethylamine were added. The solution which formed was concentrated in vacuo and the residue was taken up in acetone. The triethylammonium chloride which had separated out was filtered off and the filtrate was concentrated in vacuo. The crystalline residue was washed with water and dried. Recrystallization from diisopropyl ether gave 18 g (68% of theory) of 5-chloro-2-methylamino-1,3,4-thiadiazole of melting point 88° C.

(b) (3)

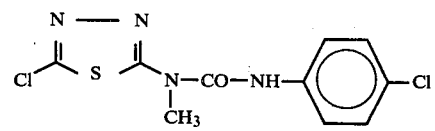

3.1 g (0.02 mol) of 4-chlorophenyl isocyanate in 100 ml of acetonitrile were added dropwise to 3 g (0.02 mol) of 5-chloro-2-methylamino-1,3,4-thiadiazole in 100 ml of acetonitrile. After adding 0.1 ml of triethylamine, the mixture was heated under reflux for 3 hours. The crystalline precipitate was filtered off and dried. This gave 5.3 g (88% of theory) of 1-(5-chloro-1,3,4-thiadiazol-2-yl)-1-methyl-3-(4-chlorophenyl)-urea of melting point 250° C.

The following compounds in Table 1 were obtained by procedures analogous to those given above:

Table 1

(I)

| Compound | $R^1$ | $R^2$ | X | Melting point (°C.) |
|---|---|---|---|---|
| 4 | CH$_3$ | –C$_6$H$_5$ | H | 146 |

Table 1-continued $$\underset{X}{\overset{N=N}{\parallel}}\underset{S}{\overset{}{\diagdown}}\underset{R^1}{\overset{}{\diagup}}N-CO-NH-R^2 \quad (I)$$

| Compound | R¹ | R² | X | Melting point (°C.) |
|---|---|---|---|---|
| 5 | CH₃ | 2-Cl, 5-CH₃-phenyl | H | 174 |
| 6 | CH₃ | 2-CH₃, 3-Cl-phenyl | H | 170 |
| 7 | CH₃ | 4-(4-Cl-phenoxy)phenyl | H | 95 |
| 8 | CH₃ | 3-Cl-phenyl | H | 182 |
| 9 | CH₃ | 2-Cl-phenyl | H | 114 |
| 10 | CH₃ | 4-NO₂-phenyl | H | 230 |
| 11 | CH₃ | 3-CF₃-phenyl | H | 168 |
| 12 | CH₃ | 3,4-Cl₂-phenyl | H | 230 |
| 13 | CH₃ | 2,5-Cl₂-phenyl | H | 230 |
| 14 | CH₃ | 2,5-Cl₂-phenyl | H | 164 |
| 15 | CH₃ | 3-CH₃, 4-Cl-phenyl | H | 176 |
| 16 | CH₃ | 3-NO₂-phenyl | H | 240 |
| 17 | CH₃ | 3-CH₃, 4-Cl-phenyl | H | 150 |
| 18 | CH₃ | 3-CH₂Cl-phenyl | H | 198 |
| 19 | CH₃ | 3,5-(CH₃)₂-phenyl | H | 161 |
| 20 | CH₃ | 4-CH₃-phenyl | H | 153 |
| 21 | CH₃ | 2-Cl, 5-CH₂Cl-phenyl | H | 200 |
| 22 | CH₃ | 4-(CHCl-CH₃)phenyl | H | 154 |
| 23 | CH₃ | 4-(CH=CH-COOC₂H₅)phenyl | H | 160 |
| 24 | CH₃ | CH₃ | H | 102 |
| 25 | CH₃ | 4-OC₂H₅-phenyl | H | 152 |
| 26 | CH₃ | 4-F-phenyl | H | 114 |
| 27 | CH₃ | 3,4-Cl₂, 5-CH₃-phenyl | H | 183 |
| 28 | CH₃ | 3-Cl, 4-CF₃-phenyl | H | 144 |
| 29 | CH₃ | 4-SCF₃-phenyl | H | 162 |
| 30 | CH₃ | 3-COOC₄H₉-phenyl | H | 90 |
| 31 | CH₃ | 2-Cl, 4-CF₃-phenyl | H | 156 |
| 32 | CH₃ | 3-(N(CH₃)-COOCH₃)phenyl | H | 140 |
| 33 | C₂H₅ | 4-Cl-phenyl | H | 142 |
| 34 | C₃H₇ | 4-Cl-phenyl | H | 96 |

The fungicidal activity of the compounds of this invention is illustrated by the following examples wherein the compounds according to the present invention are each identified by the number (given in brackets) from the preparative examples hereinabove.

The known comparison compounds are identified as follows:

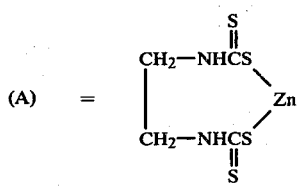

EXAMPLE 4

Seed dressing test/bunt of wheat: (seed-borne mycosis).

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10° C. in a refrigerator.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following table:

Table 2

| | Seed dressing test/bunt of wheat | | |
|---|---|---|---|
| Active Compounds | Active compound concentration in the dressing in % by weight | Amount of dressing used in g/kg of seed | Spore germination in % |
| No dressing | — | — | >10 |
| (A) | 10 | 1 | 0.5 |
| (4) | 10 | 1 | 0.005 |
| (1) | 10 | 1 | 0.000 |
| (5) | 10 | 1 | 0.05 |
| (6) | 10 | 1 | 0.05 |
| (9) | 10 | 1 | 0.05 |
| (11) | 10 | 1 | 0.05 |
| (13) | 10 | 1 | 0.005 |
| (15) | 10 | 1 | 0.05 |
| (17) | 10 | 1 | 0.05 |
| (19) | 10 | 1 | 0.05 |
| (20) | 10 | 1 | 0.000 |
| (26) | 10 | 1 | 0.005 |
| (31) | 10 | 1 | 0.05 |

EXAMPLE 5

Seed dressing test/bunt of wheat/field experiment: (seed-borne mycosis).

To produce a suitable dry dressing, the active compound was extended with a mixture of equal parts by weight of talc and kieselguhr to give a finely powdered mixture with the desired concentration of the active compound.

Dressing was carried out in 4 individual portions, each of 100 g, which were sown on 4 plots each of 5 m². The quoted infection percentages were obtained by completely counting all the diseased panicles on the individual plots and estimating the total number of all panicles by counting the panicles of a few plots with apparently the same crop density.

To test the action against bunt of wheat (*Tilletia caries*), winter wheat (certified seed) was used, which had beforehand been contaminated with 2 g of chlamydospores per kg of seed. Dressing: beginning of October; sowing: 10th–20th October; evaluation: end of June to middle of July.

The percentages of diseased panicles were in each case based on about 2,000 panicles per plot, that is, in total, on about 8,000 panicles per item of the experiment.

The active compounds, active compound concentrations in the dressing, amount of dressing used and number of diseased panicles can be seen from the table which follows.

Table 3

| | Seed dressing test/bunt of wheat/field experiment | | |
|---|---|---|---|
| Active compounds | Active compound concentration in the dressing in % by weight | Amount of dressing used in g/kg of seed | Smutted heads in % |
| No dressing | — | — | 68.91 |
| (A) | 60 | 2 | 7.41 |
| (1) | 25 | 2 | 0.00 |
| | 10 | 2 | 0.23 |

EXAMPLE 6

Pellicularia test

Solvent: 11.75 parts by weight of acetone
Dispersing agent: 0.75 part by weight of alkylaryl polyglycol ether
Water: 987.50 parts by weight The amount of active compound required for the desired concentration of active compound in the spray liquor was mixed with the stated amount of the solvent and of the dispersing agent and the concentrate was diluted with the stated amount of water.

Rice plants about 2–4 weeks old were sprayed with the spray liquor until dripping wet. The plants remained in a greenhouse at temperatures of 22° to 24° C. and a relative atmospheric humidity of about 70% until they were dry. The plants were infected with a culture of *Pellicularia sasakii* grown on malt agar and were set up at 28° to 30° C. and 100% relative atmospheric humidity.

The infection at the leaf sheaths after 5 to 8 days was determined, in relation to the untreated but infected control. The evaluation was made on a scale from 1 to 9. 1 denoted 100% action, 3 denoted good action, 5 denoted moderate action and 9 denoted no action.

The active compounds, the concentrations of the active compounds and the results can be seen from the table which follows.

Table 4

| | *Pellicularia* test |
|---|---|
| Active compound | Action at an active compound concentration (in %) of 0.025 |
| (A) | 9 |
| (19) | 3 |
| (2) | 3 |

Table 4-continued

| Active compound | *Pellicularia* test Action at an active compound concentration (in %) of 0.025 |
| --- | --- |
| (29) | 5 |
| (30) | 2 |

It will be appreciated that the instant specification and examples are set forth by way of illustration and not limitation, and that various modifications and changes may be made without departing from the spirit and scope of the present invention.

What we claim is:

1. 1-Methyl-1-(1,3,4-thiadiazol-2-yl)-3-(3-butoxycarbonylphenyl)-urea of the formula

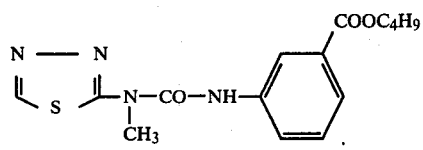

2. A fungicidal composition containing as active ingredient a fungicidally effective amount of a compound according to claim 1 in admixture with a diluent.

3. A method of combating fungi which comprises applying to the fungi, or to a habitat thereof, a fungicidally effective amount of a compound according to claim 1.

* * * * *